(12) United States Patent
Hayashi et al.

(10) Patent No.: US 6,969,820 B2
(45) Date of Patent: Nov. 29, 2005

(54) MARKING METHOD AND MARKING APPARATUS USING MULTIPLE PHOTON ABSORPTION, MARKED OPTICAL ELEMENT MANUFACTURED BY USING THE MARKING METHOD AND THE MARKING APPARATUS

(75) Inventors: Ken-ichi Hayashi, Nakagun (JP); Kazuyoshi Itoh, Kawanishi (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 0 days.

(21) Appl. No.: 10/921,848

(22) Filed: Aug. 20, 2004

(65) Prior Publication Data

US 2005/0016973 A1 Jan. 27, 2005

Related U.S. Application Data

(62) Division of application No. 10/622,488, filed on Jul. 21, 2003, which is a division of application No. 09/940,604, filed on Aug. 29, 2001, now Pat. No. 6,621,041.

(30) Foreign Application Priority Data

Aug. 29, 2000 (JP) ........................................ 2000-258854

(51) Int. Cl.[7] .............................................. B23K 26/00
(52) U.S. Cl. ............................. 219/121.69; 219/121.68; 219/121.85
(58) Field of Search ....................... 219/121.69, 121.85, 219/121.68, 121.6

(56) References Cited

U.S. PATENT DOCUMENTS

| | | | | |
|---|---|---|---|---|
| 4,878,212 A | * | 10/1989 | Kuder | ........................ 369/100 |
| 6,187,213 B1 | * | 2/2001 | Smith et al. | ................... 216/28 |
| 6,303,930 B1 | | 10/2001 | Hagiwara | |
| 6,322,958 B1 | | 11/2001 | Hayashi | |
| 6,333,486 B1 | | 12/2001 | Troitski | |
| 6,392,683 B1 | | 5/2002 | Hayashi | |
| 6,417,879 B2 | | 7/2002 | Hayashi | |
| 6,501,499 B2 | | 12/2002 | Hayashi | |

FOREIGN PATENT DOCUMENTS

| | | |
|---|---|---|
| JP | 6-500275 | 1/1994 |
| JP | 7-136782 | 5/1995 |
| JP | 2810151 | 7/1998 |
| JP | 11-13896 | 1/1999 |
| JP | 11-267861 | 10/1999 |

OTHER PUBLICATIONS

Parthenopoylos et al., "Three–Dimensional Optical Storage Memory," Science, vol. 245, No. 4920, pp. 843–845, Aug. 25, 1989.

* cited by examiner

*Primary Examiner*—M. Alexandra Elve
(74) *Attorney, Agent, or Firm*—Squire, Sanders & Dempsey L.L.P.

(57) ABSTRACT

A marking method is provided which permits an easy detecting of the presence of a mark without using a specific reading apparatus, and is capable of avoiding a damage as well as a strength deterioration of an object material. The marking method comprises: preparing a marking object; converging, into the marking object, a laser beam having a wave length range so chosen that the laser beam can transmit through a material forming the marking object, and then effecting a multiple photon absorption; and moving a converging position of the laser beam, in a manner such that an area, whose refractive index is changed due to the multiple photon absorption, can form a diffraction pattern capable of diffracting a visible light.

2 Claims, 8 Drawing Sheets

DISPLACEMENT FROM A REFERENCE POINT IN A DIRECTION ALONG A GRATING VECTOR (μm)

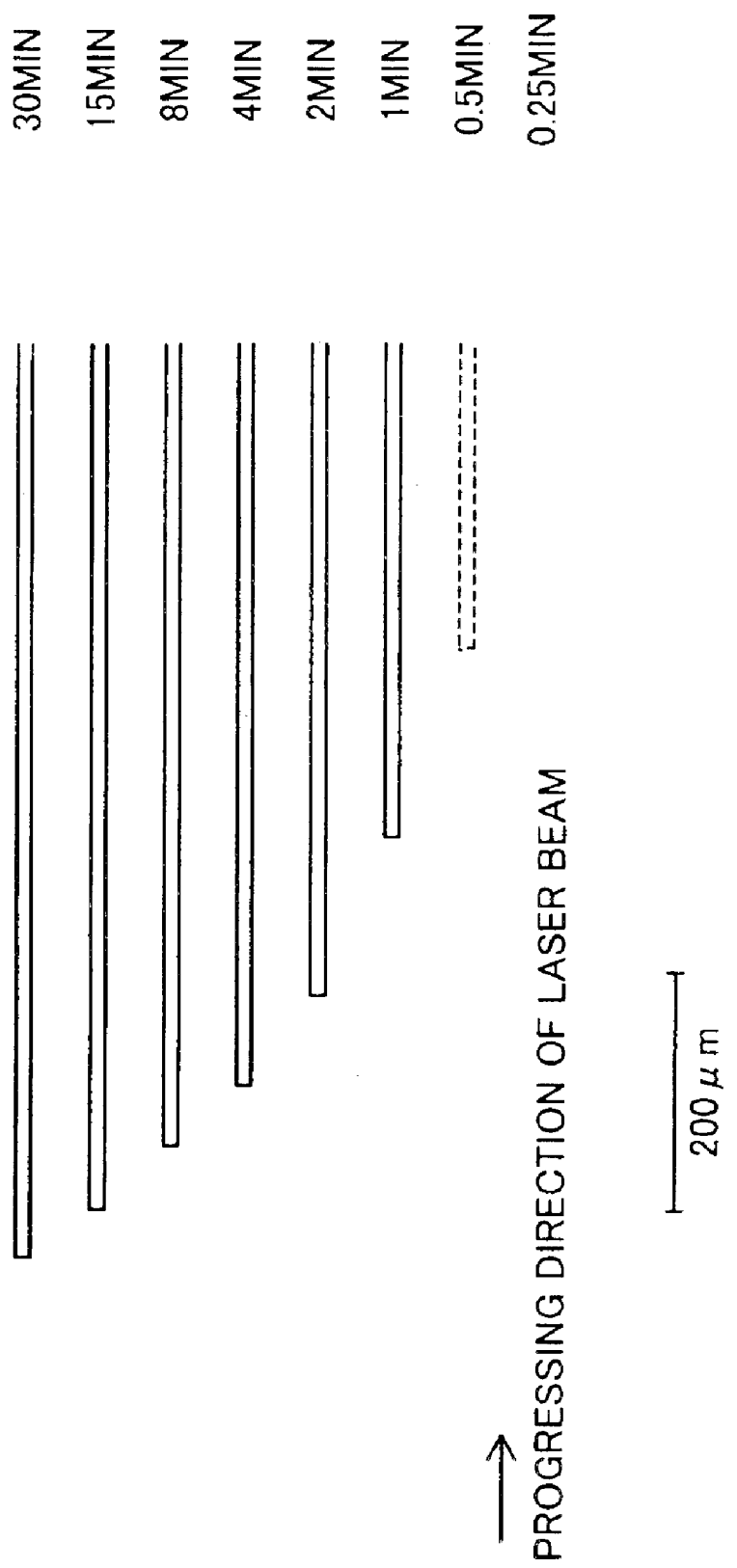

MARKING METHOD AND MARKING APPARATUS USING MULTIPLE PHOTON ABSORPTION, MARKED OPTICAL ELEMENT MANUFACTURED BY USING THE MARKING METHOD AND THE MARKING APPARATUS

This is a Divisional of application Ser. No. 10/622,488 filed Jul. 21, 2003which in turn is a Division of application Ser. No. 09/940,604, filed Aug. 29, 2001, which issued as U.S. Pat. No. 6,621,041 on Sep. 16, 2003. The disclosures of the prior applications are hereby incorporated by reference herein in their entirety.

BACKGROUND OF THE INVENTION

1. Field of the Invention

The present invention relates to a technology in which a laser beam is converged into a transparent material to change an optical property of the beam-converged portions of the material so as to form a mark within the transparent material.

2. Description of the Related Art

As a method for forming a mark within a transparent material, there have been known several processes disclosed in Japanese National Publication HEI 6-500275, JP-A HEI 7-136782 and JP Patent No. 2810151. Each of these disclosed processes is to converge a laser beam into a transparent material to form a crack within the material by virtue of a non-linear absorption effect. In this way, an opaque portion will result due to the formation of the crack, thereby forming a desired mark within the transparent material. On the other hand, in order to form a clearly visible mark in a transparent material using any one of the aforementioned processes, it is necessary to enlarge the size of a crack. However, once the crack is made large in its size, the strength of the transparent material will become low because the crack can probably extend to the surface of the transparent material, thus bringing about a damage (destruction) to the material.

In view of the above, the inventors of the present invention have tried an improved laser radiation process capable of performing a specific control of a laser beam, so that a crack is formed only in an internal position of a glass substrate even if it has a small thickness, as disclosed in JP-A HEI 11-13896.

Further, the inventors of the present invention have also developed another method which does not need to form a crack, but needs to change the refractive index of an object material so as to form a desired mark, as disclosed in JP-A HEI 11-267861. With the use of this method, since the crack is not formed, it is allowed to further reduce the possibility of causing a damage to an object material, as compared with the aforementioned method disclosed in JP-A HEI 11-13896.

However, in a process for carrying out the above method using a change in the refractive index, a mark will become extremely small in its size. As a result, a specific reading apparatus will become necessary to detect the presence of the small mark. Namely, although the aforementioned method can be suitably used to form a "hidden mark," it is not suitable for general use in forming a common mark.

SUMMARY OF THE INVENTION

Accordingly, it is an object of the present invention to provide an improved marking method and an improved marking apparatus, capable of easily detecting the presence of a mark without using a specific reading apparatus, also capable of avoiding a damage as well as a strength deterioration of an object material. It is another object of the present invention to provide an indication apparatus in which marks are formed by using the use of the improved method and the improved apparatus.

According to one aspect of the present invention, there is provided a marking method comprising the steps of: preparing a marking object; converging, into the marking object, a laser beam having a wave length range so chosen that the laser beam can transmit through a material forming the marking object, and then effecting a multiple photon absorption; and moving a converging position of the laser beam, in a manner such that an area, whose refractive index is changed due to the multiple photon absorption, can form a diffraction pattern capable of diffracting a visible light.

According to another aspect of the present invention, there is provided a marking apparatus comprising: a stage for mounting a marking object; a light source for producing a laser beam having a wave length range so chosen that the laser beam can transmit through a material forming the marking object; an optical system for converging the laser beam emitted from the light source into the marking object, then effecting a multiple photon absorption; and a moving mechanism for moving the converging position in a manner such that characteristic-changed portions formed by virtue of the multiple photon absorption, will form, in the converging positions of the laser beam, a diffraction grating capable of diffracting a visible light.

The above method and the above apparatus involve converging, into the marking object, a laser beam having a wave length range so chosen that the laser beam can transmit through a material forming the marking object, and then effecting a multiple photon absorption. As a result, even if a laser beam has a relatively low photon energy, provided that such a laser beam is used and thus a light converging spot is formed within the marking object, it is still possible to effect a large change in an optical property (such as refractive index) of the marking object. Such change in an optical property is different from an occurrence of crack, so that it does not bring about any damage to the marking object or cause any deterioration in its strength. Further, since the above method ensures that an area with its refractive index changed can diffract a visible light, a mark formed within the marking object can be macroscopically recognized according to changes in brightness or darkness as well as changes in color. As a result, such a mark is easily visible.

According to a further aspect of the present invention, there is provided an optical element formed by a material capable of transmitting therethrough a visible light and containing a pattern consisting of different portions having different optical properties, wherein said pattern is capable of diffracting a visible light.

By virtue of diffraction of visible light, it is possible to visualize, according to changes in brightness or darkness as well as changes in color, a mark consisting of a pattern formed by portions of which different optical properties are changed. In practice, such a mark can be used as a mark identifying an apparatus. Further, it is also possible to manufacture an optical element having a colorful mark, as if it is an ornamental article.

According to a still further aspect of the present invention, there is provided a marking method comprising: a first step of irradiating a marking object by a pulse laser beam while at the same time changing NA of an objective lens and an energy per pulse, thereby forming a characteristic-changed area by virtue of movement of a light converging spot; a second step of obtaining a relationship among the length of the characteristic-changed area, an NA and an energy per pulse; a third step of determining the length of a characteristic-changed area to be formed; a fourth step of determining an NA and an energy per pulse, in accordance with the relationship obtained in the second step, also in accordance with the length of a characteristic-changed area to be formed; and a fifth step of converging a laser beam on the marking object to form a characteristic-changed area therein, by using the determined NA and the determined energy per pulse.

In this way, by properly selecting an NA and an energy per pulse, it is possible to form a characteristic-changed area having a desired length.

BRIEF DESCRIPTION OF THE DRAWINGS

FIG. 8 is an enlarged front view showing some characteristic-changed areas formed by changing the length of an exposure time.

DETAILED DESCRIPTION OF THE PREFERRED EMBODIMENTS

A marking method and a marking apparatus formed according to an embodiment of the present invention will be described in detail below with reference to the accompanying drawings.

Figure 1:
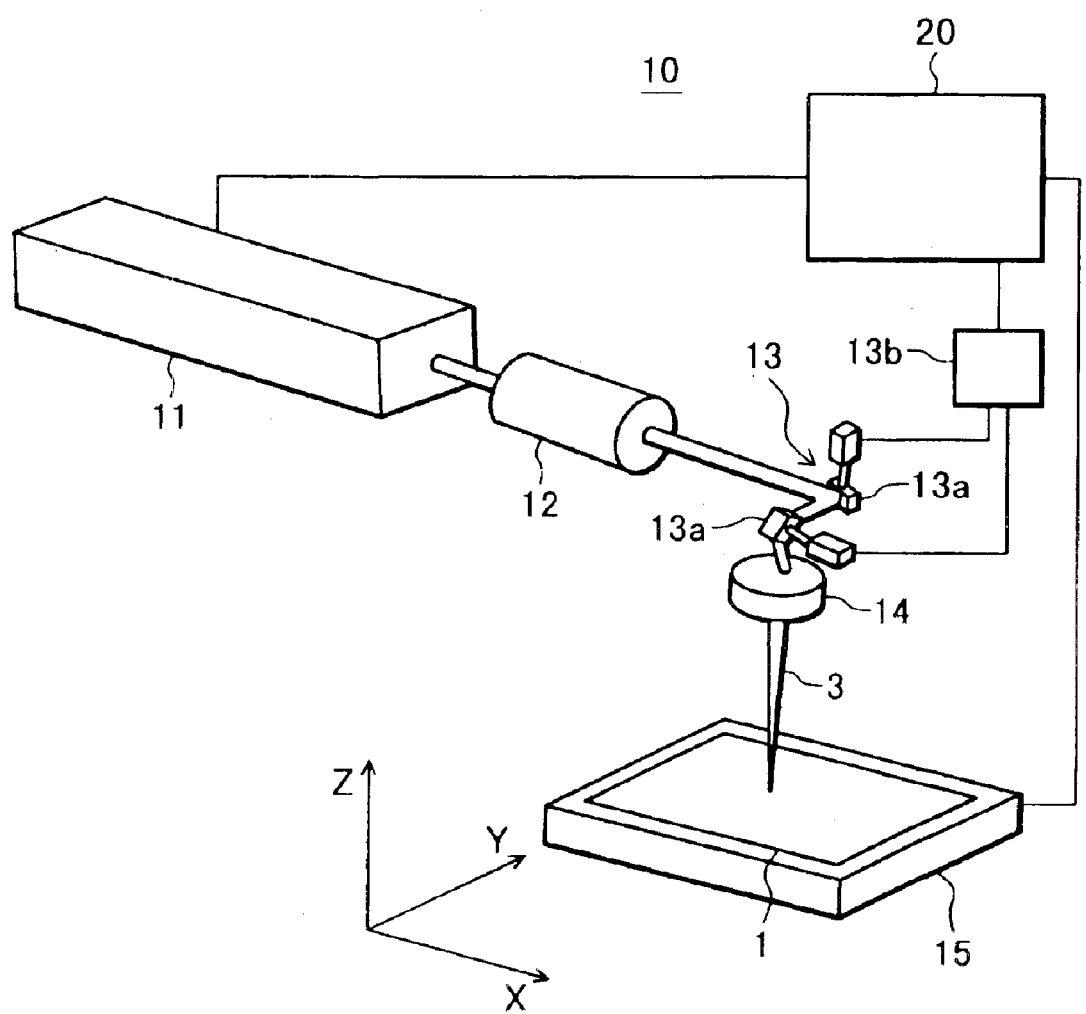
FIG. 1 is an explanatory view schematically showing a marking apparatus for carrying out a marking method for forming a mark in a light transmissible material, according to an embodiment of the present invention.

FIG. 1 is a perspective view schematically showing a marking apparatus 10 formed according to one embodiment of the present invention. As shown in the drawing, the marking apparatus 10 comprises a laser beam source 11 for emitting a laser beam having a predetermined wave length range and capable of passing through a transparent glass substrate 1 (serving as an object material for marking treatment), a beam shaper 12 for trimming the shape of the laser beam emitted from the laser beam source 11, a galvano-scanner 13 for moving the laser beam's converging position (formed in the transparent glass substrate 1) along a trace forming a predetermined pattern, an fθ lens 14 for converging the laser beam in a desired depth within the transparent glass substrate 1, and a stage 15 for mounting the transparent glass substrate 1 and for properly moving the substrate in an XY plane.

For use as the laser beam source 11, it is allowed to employ a mode-locked Ti:sapphire laser. Thus, the laser beam source 11 is adapted to produce a pulse-shaped laser beam having a pulse width of 130 fs, a wavelength of 800 nm, an average output of 1 W, and a cyclic frequency of 1 kHz. Further, for use as the laser beam source 11, it is also possible to employ a laser diode (LD) exciting type solid laser oscillator such as YAG laser or YLF laser. Moreover, it is allowed to use various other types of laser beam sources each capable of producing a harmonic component generated from a fundamental component outputted from a laser oscillator.

The galvano-scanner 13 includes a mirror driving device for rotatably driving a pair of galvano mirrors 13a, also includes a position detecting device for detecting a high brightness position. In this way, it is possible to move the beam spot (formed in the transparent-glass substrate 1 by virtue of the fθ lens 14) to any optional point in the XY plane. Furthermore, the galvano-scanner 13 itself is controlled by a computer 20 though a driving section 13b. The computer 20 synchronizes the move of the galvano-scanner 13 with the pulse oscillation of the laser beam source 11.

The fθ lens 14 is adapted not only to converge the laser beam in the transparent glass substrate 1, but also to keep the beam spot of the laser beam at a constant depth during a scanning operation using the galvano-scanner 13. On the other hand, instead of operating the stage 15 to move the transparent glass substrate 1 in the Z direction, it is of course also possible to move the fθ lens 14 in the Z direction so as to obtain the same effect as to move the stage 15 in the Z direction.

In this manner, a characteristic-changed portion, at which the refractive index is changed, can be formed at the light converging spot of the laser beam (which is formed by virtue of the fθ lens 14). Using the galvano-scanner 13 to scan the light converging spot, it is possible to form a desired pattern consisting of the characteristic-changed portions. When such a pattern forms a diffraction grating capable of diffracting a visible light, the pattern can be easily visualized by virtue of a diffracted light.

The stage 15 is adapted to adjust a mark formation position by moving the transparent glass substrate 1 to any optional position along the XY plane. By driving the galvano-scanner 13, each unit diffraction pattern consisting of a characteristic-changed portion can thus be formed. Therefore, by properly driving the stage 15, a plurality of unit diffraction patterns may be formed in any optional positions within the transparent glass substrate 1. In this way, it is allowed to form an indication apparatus with a mark formed inside it for indicating a figure, a character or a symbol. The operation of the stage 15 is controlled by the computer 20 so as to be synchronous with the move of the galvano-scanner 13 as well as the move of the laser beam source 11.

Furthermore, the stage 15 can also operate to slightly move the transparent glass substrate 1 in the Z direction. This has been proved effective for adjusting the depth of each mark formed within the transparent glass substrate 1. For example, if a first mark is formed at a first depth inside the transparent glass substrate 1, and a second mark is formed at a second depth inside the transparent glass substrate 1, it is permitted to form a total mark having a multi-layered structure. In addition, if the galvano-scanner 13 is operated to form diffraction marks and at the same time the stage 15 is moved step by step in a three-dimensional space, it is possible to form a stereoscopically arranged mark.

The transparent glass substrate 1 can be any sort of material, provided that it can transmit therethrough a laser beam emitted from the laser beam source 11, and can cause an effective multiple photon absorption of the laser beam. Further, in order to visualize each diffraction mark formed within the transparent glass substrate 1, the transparent glass substrate is required to transmit therethrough almost all the visible lights. For example, it is allowed to use a $GeO_2$—$SiO_2$ glass. In fact, it has been confirmed that it is possible to form diffraction marks in various sorts of glass materials including Soda lime glass and a quartz glass.

An operation of the apparatus shown in FIG. 1 will be described below with reference to the accompanying drawings. At first, the transparent glass substrate 1 is mounted on the stage 15, and the substrate's one portion to be formed with a diffraction mark is moved to a position right under the fθ lens 14 (step S1).

Then, the galvano-scanner 13 is operated synchronously with the laser beam source 11 so as to scan the light converging point of the laser beam (step S2). At this time, since the laser beam source 11 produces extremely short pulses in a femto-second order, a sort of phenomenon called multiple photon absorption will effectively occur at each light converging point. If such kind of multiple photon absorption is fully utilized, it will be possible to effect an energy injection by virtue of an infrared laser beam which is not essentially absorbed. In this way, it is allowed to effect a relatively large change in an optical property (such as refractive index) at each light converging point, but not in any other positions. Such kind of an optical property change is an optical non-linear phenomenon caused due to a density change in the transparent glass substrate 1 or due to a change in its bonding state, thereby forming characteristic-changed portions permanently remaining in the transparent glass substrate. As a result, these characteristic-changed portions can thus be formed in the transparent glass substrate 1 along the scanning trace of the galvano-scanner 13.

Therefore, if the laser beam is caused to perform the scanning in a manner such that the characteristic-changed portions will form a Bragg diffraction grating, the Bragg diffraction grating can thus be formed without any difficulty. When a visible light is incident into the diffraction grating, a light diffracted in a direction corresponding to grating intervals is then emitted out. For example, when the diffraction grating is irradiated by a white light and then observed while varying from visual angle, a mark can be seen as changing in rainbow colors. On the other hand, when the diffraction grating is irradiated by a single color light, a light diffracted at a specific angle corresponding to the wavelength of the single color light is thus emitted. Further, if the emitted light is observed through a filter which allows the passing of only the single color light, it is possible to detect the mark with a high S/N ratio. A contour for the scanning area forming the diffraction grating should not be limited to a rectangular shape, it is in fact also possible to form other shape such as a circular shape.

After that, the scanning of the laser beam is stopped temporarily, while the stage 15 is operated to move the transparent glass substrate 1. In this manner, the light converging spot of the laser beam can be moved to a position necessary for forming the diffraction grating, (step S3).

Similar to the step S2, the galvano-scanner 13 and the laser beam source 11 are operated synchronously with each other, so as to scan the light converging spot of the laser beam. Accordingly, a diffraction grating can be formed at the position (step S4).

By repeating the above step S3 and the step S4, a plurality of diffraction gratings can be successively formed in desired positions. As a result, it has become possible to form in the transparent glass substrate 1 a mark which can be recognized as a figure, a character or a symbol. In practice, such kind of a mark can be present in any optional pattern, provided that it is visually recognizable. For example, it may be an identification code or simply an ornament which itself has not any meaning.

Although the marking apparatus shown in FIG. 1 is so formed that the galvano-scanner 13 is operated to scan the laser beam in a direction towards the inner layer of the transparent glass substrate 1, it is also possible to use a driving system of the stage 15 to scan the laser beam, instead of using the galvano-scanner 13. At this time, since it is not necessary to operate the galvano-scanner 13, it is allowed to replace the galvano-scanner 13 with a stationary mirror. Further, it is also allowed to replace the fθ lens 14 by a common objective lens such as a microscope objective lens. It is preferable to operate the driving system of the stage 15 at a high speed and with a high precision.

In addition, it is also possible that both the galvano-scanner 13 and the driving system of the stage 15 may be used to scan the laser beam so as to form a diffraction grating. At this time, a relatively high speed scanning using the galvano-scanner 13 can serve as a main scanning, while a relatively low speed scanning using the driving system of the stage 15 can serve as a sub-scanning.

In the following, description will be given to explain in detail an example about how to form a mark in an object material in the following example, only the driving system of the stage 15 is used to scan the laser beam to form a diffraction mark. Further, instead of using the fθ lens 14, a microscope objective lens was used which has a focus distance of 10 mm and a numeral aperture (NA) of 0.23. An energy per pulse of a laser beam passing through the lens is about 0.2 to 0.4 µJ/pulse.

Figure 2A:
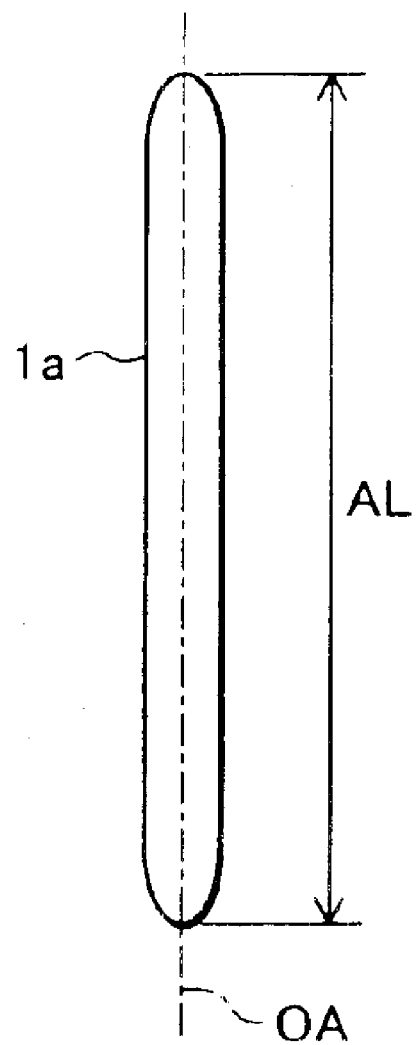
FIG. 2A and FIG. 2B are a side view and a front view schematically showing a characteristic-changed portion formed by using the apparatus of FIG. 1.
Figure 2B:
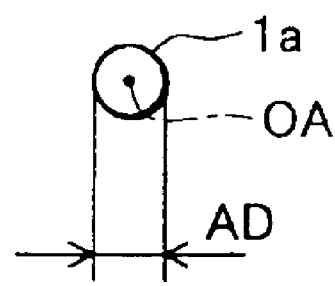

FIGS. 2A and 2B are a side view and a front view schematically showing a characteristic-changed portion formed around focus by virtue of a single pulse laser beam. FIG. 2A is a side view in which a characteristic-changed portion is viewed in a direction perpendicular to the optical axis. FIG. 2B is a front view in which the characteristic-changed portion is viewed in the direction of the optical axis. As shown in these views, an intensity distribution of a laser beam in its cross section is infinite-fold rotation symmetrical with respect to the optical axis OA. A characteristic-changed area 1a obtained in the present embodiment is a bar-like area along the optical axis OA, having a diameter AD of about 1 µm and a length of about 20 to 30 µm.

Here, although the focus depth of the converging lens is 5 µm, the characteristic-changed area 1a is extending for 30 µm along the optical axis. A reason for this may be that a self converging effect obtainable by an optical Kerr-effect matches a diffraction effect. An alternative reason may be that the self converging effect is occurring due to a thermal non-linear property.

Next, another embodiment will be described in which a light converging condition for converging a laser beam has been changed so as to be different from the above first embodiment. When a laser beam having an energy per pulse of 2 µJ/pulse is incident through a lens having a focus distance of 100 mm and an NA of 0.05, it was found that a characteristic-changed area was formed which has a length of 500 µm and a diameter of 1 to 2 µm. The laser used here is Ti:sapphire laser having a cyclic frequency of 1 kHz, a wavelength of 800 nm and a pulse width of 130 fs.

For reference, after a pulse laser beam is converged into the transparent glass substrate, its temperature rising is calculated, so as to carry out an evaluation on the self converging effect obtained in the present embodiment. For calculating the temperature rising, the following three-dimensional heat diffusion equation (1) was analyzed.

$$\partial u/\partial t = a\{(\partial^2/\partial x^2)u + (\partial^2/\partial y^2)u + (\partial^2/\partial z^2)u\} \quad (1)$$

Here, u is temperature, t is time and a is diffusion coefficient. An energy absorption of the laser pulse will happen in accordance with Lambert-Beer Law, with an initial temperature distribution assumed to be a Gauss distribution. Specifically, when t=0, temperature u was set at 10° K, and a thermal temperature coefficient of the glass substrate was set at $10^{-7}$ or less. At this time, since the cyclic frequency of the laser pulse was 1 kHz, a pulse interval was set to be 1 ms. As a result of a calculation, it was found that at a time which was 1 ms after an irradiation using a pulse laser beam having a pulse width of 130 fs, a residue temperature rising was about 10° C. Consequently, when there are a plurality of incident pulses, a thermal self converging effect becomes important.

Figure 3:
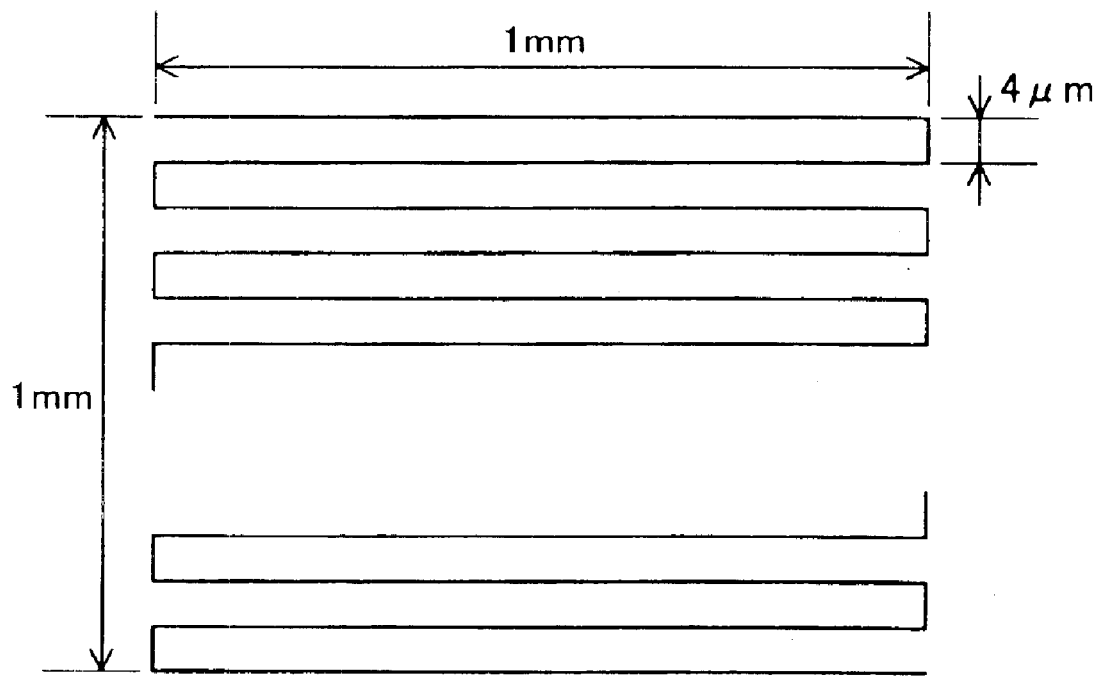
FIG. 3 is an explanatory view schematically showing a scanning pattern of a laser beam.

FIG. 3 shows the trace traveled by the converging spot of the laser beam when the stage 15 is actuated. The lateral direction of FIG. 3 is a main scanning direction, while the longitudinal direction of the figure is a sub-scanning direction. The speed of the main scanning is 0.1 mm/s and a scanning line interval (a pitch of sub-scanning) is 4 µm. By virtue of these scannings, a Bragg diffraction grating is formed in a square area of 1 mm×1 mm.

Since the main scanning speed is 0.1 mm/s, an interval in the main scanning direction of a characteristic-changed area will be 0.1 µm. Further, since the diameter of a characteristic-changed area formed during one shot is 1 to 2 µm, an entire characteristic-changed area can be arranged to be continuous in the main scanning direction.

Figure 4A:
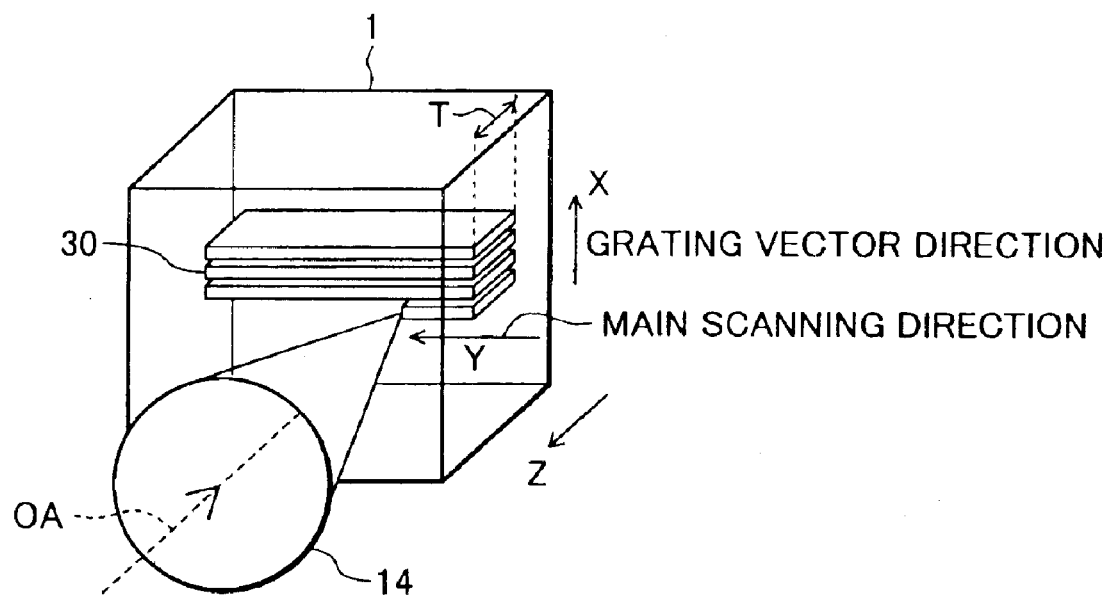
FIG. 4A and FIG. 4B are perspective views schematically showing the structure of Bragg diffraction grating formed within a glass substrate.
Figure 4B:
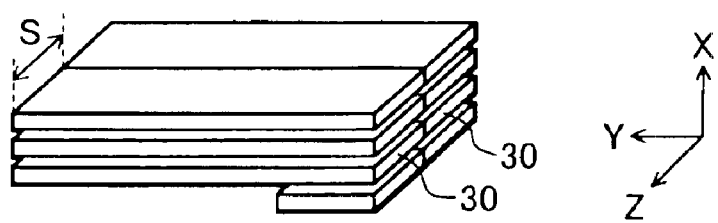

FIG. 4 shows a diffraction grating to be formed in a scanning area within the transparent glass substrate 1. FIG. 4A shows a process for producing a first layer Bragg diffraction grating 30. FIG. 4B is used to show a process for producing a second layer Bragg diffraction grating 30. Furthermore, it is allowed to consider establishing an XYZ coordinate system in which X axis represents a grating vector direction of a diffraction grating, while Y axis represents a main scanning direction of the converging spot of the laser beam.

In fact, the diffraction grating is formed by the Bragg diffraction grating 30 having a two-layer structure formed by two grating layers arranged in the Z direction. The thickness T of the first layer Bragg diffraction grating 30 is 30 µm. A positional deviation S in the optical axis direction (Z direction) between the first layer Bragg diffraction grating 30 and the second layer Bragg diffraction grating 30 is approximately equal to the thickness T, i.e., about 30 µm. If the first layer diffraction grating 30 is translated by a distance S in the Z direction towards the second layer diffraction grating, the first layer diffraction grating will become overlapped with the second layer diffraction grating. In this way, it is possible to obtain a diffraction grating having a thickness of 60 µm. The diffraction efficiency of an obtained diffraction mark was ten-odd percent.

In the following, description will be given to explain a refractive index change occurred in the Bragg diffraction grating 30. In fact, using Kogelnik Combination Mode Theory, it is possible to obtain the following equation (2) so as to evaluate an intensity of the refractive index change.

$$\eta = \sin^2(\pi n_1 T/\lambda_0 \cos \theta_B) \quad (2)$$

Here, η represents a diffraction efficiency, $n_1$ represents an intensity of a refractive index change, T represents a thickness of a grating, $\lambda_0$ represents a wave length of an incident beam, $\theta_B$ represents a Bragg angle. A Bragg condition can be obtained by $$K_S = K_I + K \quad (3)$$

Here, $K_S$ represents a diffraction wave number vector, $K_I$ represents an incident wave number vector, K represents a grating vector.

A refractive index distribution is assumed to be a sine wave-like distribution according to the above theory. However, the refractive index change of the grating thus formed is different from the sine wave, forming a wave of comb tooth function. This is because a refractive index change resulting from a laser pulse is located in the vicinity of the converging spot of a laser beam. In the present evaluation, the grating thus formed was supposed to be an overlap with a diffraction grating having a sine wave-like shape. The refractive index change n(x) may be represented by the following equation.

$$n(x) = (\Sigma^m_{L=1} n_L \cos (L\pi x/\Lambda) \quad (4)$$

Here, m is an integer number, x is a coordinate along the direction of a diffraction grating vector, $n_L$ represents an amplitude of a sine wave-like refractive index diffraction grating, 2Λ represents a period of each diffraction grating.

The refractive index distribution was evaluated by using the above equations (2), (3) and (4). Usually, since the refractive index change is small (approximately $10^{-3}$), Born primary approximation was used. During such primary approximation, it is assumed that the light beam diffracted by one grating will not be diffracted by the other grating. An He—Ne laser beam was used as an incident light and an incident angle was changed, thereby obtaining a high order diffracted beam. In this way, it was able to observe a fifthly diffracted light beam. Nevertheless, since an intensity of a high order (higher than tertiary) diffracted light beam is less than 0.1% of a zero order diffracted light beam, the above equation (4) has been established to include at most tertiary diffracted light beam.

The following Table 1 is used to show measurement results obtained in different steps for manufacturing only the first layer Bragg diffraction grating 30.

TABLE 1

| *I* | Diffraction Efficiency (%) | Refractive Index Change (x$10^{-3}$) |
|---|---|---|
| 1 | 3.3 | 1.22 |
| 2 | 1.4 | 0.78 |
| 3 | 0.12 | 0.22 |

Figure 5:
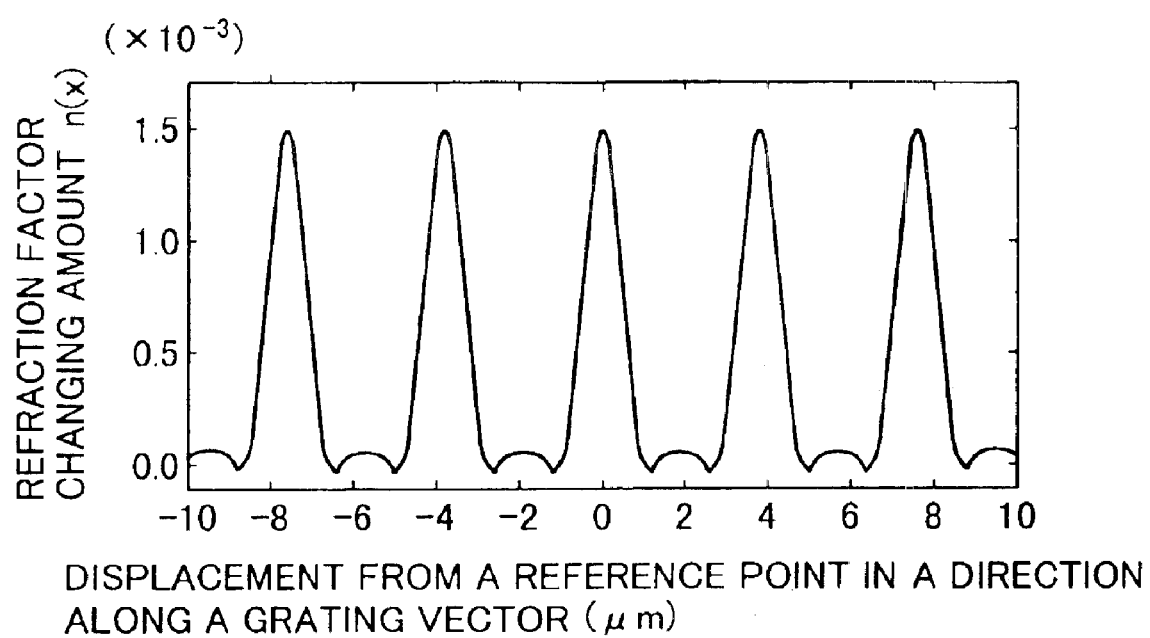
FIG. 5 is a graph showing a change in the diffraction factor of the Bragg diffraction grating shown in FIG. 4A and FIG. 4B.

FIG. 5 shows an evaluated distribution of the refractive index change. The horizontal axis is plotted to represent (using a unit "µm") a displacement from a reference point along a grating vector. The vertical axis is plotted to represent a change n(x) in the refractive index. FIG. 5 indicates that a changing amount of refractive index will become $1.5 \times 10^{-3}$, and that a total scattering loss of the formed diffraction grating will become 15%. Here, it is allowed to consider that a large scattering loss and a low diffraction efficiency are all caused due to a heterogeneity such as a local damage or a void. Thus, it can be considered that in the surrounding areas around a void, an increase in the density of a glass substrate causes an increase in the refractive index, and that in the areas within the void, the refractive index becomes low. A refractive index change evaluated in the present experiment may be considered to be an average value obtained by averaging the refractive indexes of void portions and the refractive indexes of areas not involving the voids but involving only a change in the refractive index.

The above equation (2) indicates that an increase in the thickness of a diffraction grating causes an increase in the diffraction efficiency. The thickness of the diffraction grating can be increased by moving a light converging spot along the optical axis so as to manufacture a diffraction grating having a two-layer structure (refer to FIG. 4B). At this time, the diffraction efficiency of a primary diffracted light beam was found to have been increased to 13%.

Although in the above-described embodiment, the pitch of the Bragg diffraction grating 30 is fixed at 4 $\mu$m, such a diffraction grating pitch may be formed by performing a periodic modulation. For example, a modulation may be performed in a manner such that a pitch will be gradually increased, such as 4 $\mu$m, 5 $\mu$m, 6 $\mu$m and 7 $\mu$m, . . . and it is also possible to perform a modulation in a manner such that the pitch will be periodically changed, such as 4 $\mu$m, 5 $\mu$m, 4 $\mu$m and 5 $\mu$m.

Although in the above embodiment it has been described that a diffraction grating may be a Bragg diffraction grating, it is also possible to use (for example) a Fresnel zone plate rather than the Bragg diffraction grating. Therefore, it is possible to form a constant bright/dark pattern. Further, the diffraction grating has-been made not only visible, but also functional as a beam splitter for separating a specific light component having a specific wavelength (color).

In the following, description will be given to explain an example for manufacturing a Fresnel zone plate. Such a zone plate is adapted to converge a divergent beam, which is propagating apart from the optical axis, on a spot of the optical axis. The width $\Lambda_L$ of L-th zone may be obtained according to the following equations.

$$\Lambda_L = \lambda/(2 \sin \theta_L)$$

$$\theta_L = \tan^{-1}(r_L/f) \qquad (5)$$

Figure 6A:
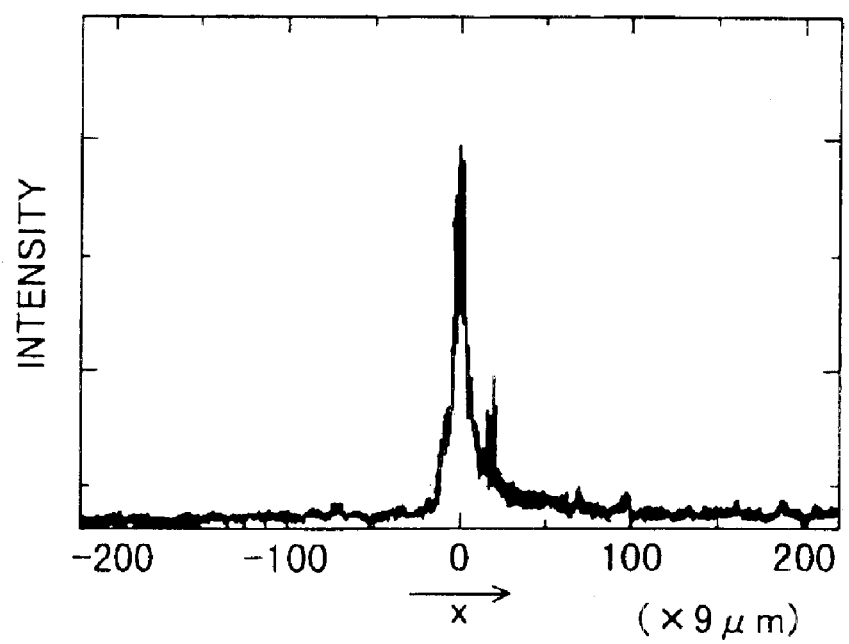
FIG. 6A and FIG. 6B are graphs showing a light converging on a Fresnel zone plate.
Figure 6B:
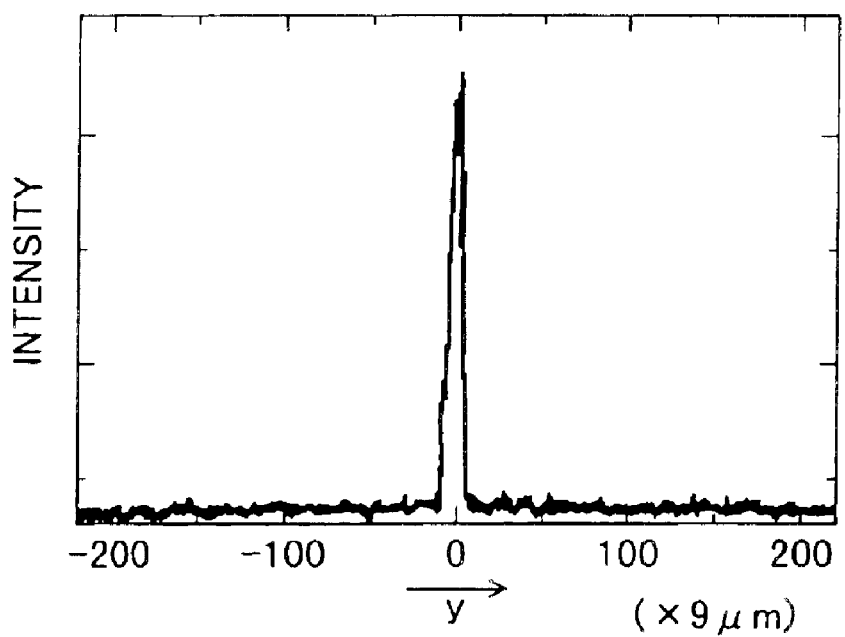

Here, $\theta_L$ represents an L-th diffraction angle, $\lambda$ represents the wave length of an incident light beam, $r_L$ represents an outer radius of an L-th zone, f represents a distance between the Fresnel zone plate and the light converging point. In the present experiment, $\lambda$=633 nm, f=50 mm, $r_L$=4–5 mm, and period $\Lambda_L$ was set to be 4.0–3.2 $\mu$m. The size of the zone plate was 1 mm×1 mm. The He—Ne laser beam (having a wave length of 633 nm) diverging from a lens is caused to irradiate the zone plate, thereby converging a diffracted light (whose NA is 0.1) on the light receiving surface of CCD. FIG. 6A and FIG. 6B show intensity distributions of the light converging points on both the X direction cross section and the Y direction cross section. The diameter of the laser beam spot was about 80 $\mu$m, its diffraction efficiency was 2.9%. Due to an aberration of the zone plate having a relatively large thickness, a diffraction limiting, operation (about 4 $\mu$m) could not be effected.

Figure 7:
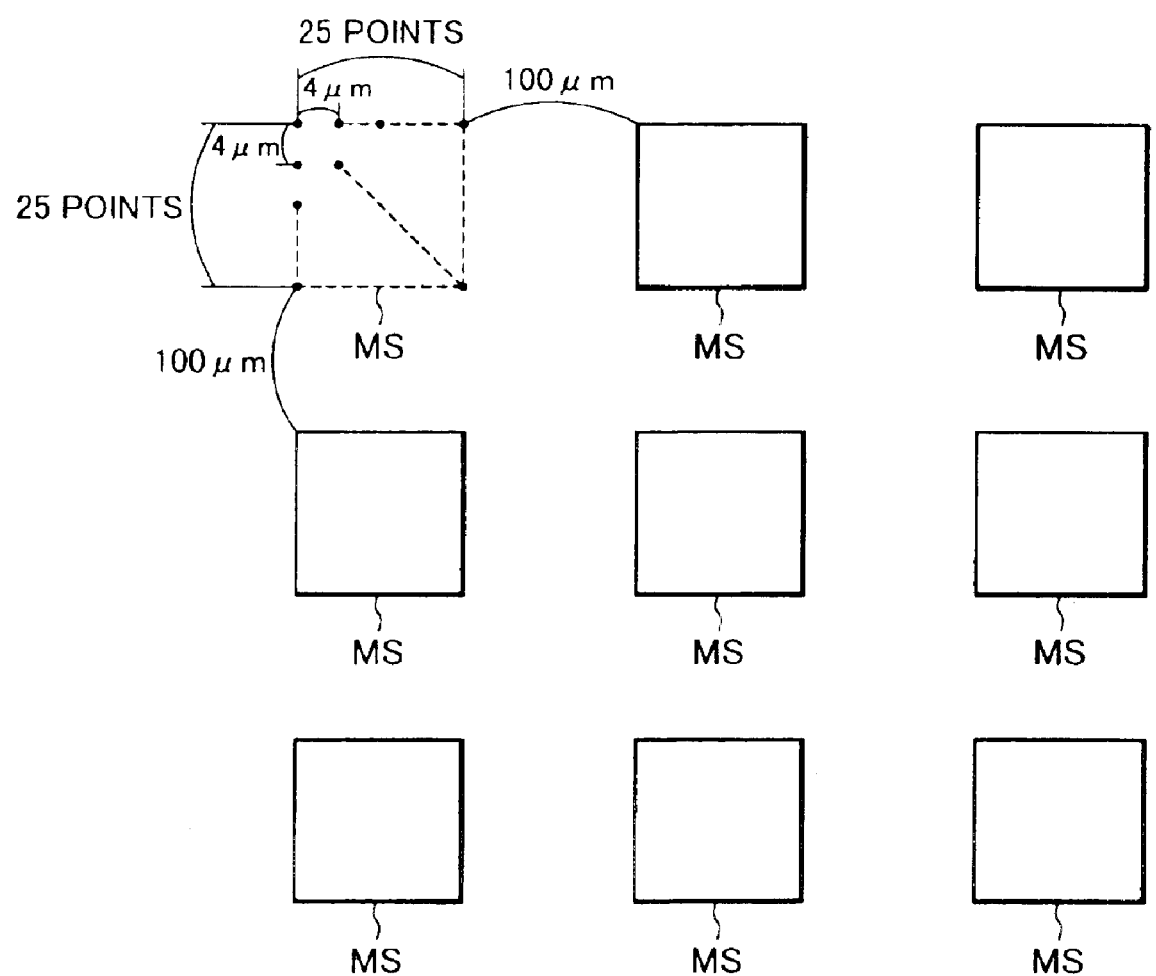
FIG. 7 is an explanatory view showing a diffraction pattern comprising a spot array.

In the following, description will be given to explain a diffraction grating formed by spot array. FIG. 7 is a plan view conceptively showing an arrangement of spot array which has been manufactured. A plurality of matrixes MS each comprising 25×25 at a pitch of 4 $\mu$m are prepared, and the prepared matrixes MS are arranged into an array of 3×3 at a pitch of 200 $\mu$m, thereby obtaining the diffraction grating.

Next, description will be given to explain a condition for manufacturing the diffraction grating. In practice, a Ti:sapphire laser is used as the laser beam source 11, its cyclic frequency is 1 kHz, its wavelength is 800 nm, and its pulse width is 130 fs. The numerical aperture NA of an objective lens for converging a laser beam on the transparent glass substrate 1 is 0.3. An energy per pulse at light converging points during a writing in process is 0.68 $\mu$J/pulse, with an exposure time on each light converging point being 1 s. With the use of the diffraction grating formed in the above-described manner, it was allowed to obtain a clear visibility by virtue of a diffraction effect, as compared with the case in which only the number of marks has been increased.

Other embodiments of the present invention will be described in the following. An energy per pulse was set to be 1.9 $\mu$J/pulse, the focus distance of an objective lens was set to be 100 mm, NA was set to be 0.05, while Ti: sapphire laser was converged into a glass substrate. Cyclic frequency for pulse oscillation and wavelength were just the same as those in the above embodiment.

FIG. 8 is an enlarged front view showing some characteristic-changed areas formed by changing an exposure time. As can be seen from the drawing, if an exposure time is increased, a characteristic-changed area will extend towards the upstream side of the laser beam. On the other hand, if an exposure time was set to be 0.5 minutes, a characteristic-changed area was difficult to observe. Furthermore, if an exposure time was set to be 0.25 minutes, it was almost impossible to observe a characteristic-changed area.

Then, an irradiation time was set to be 2 minutes and an energy per pulse was changed, thereby forming a characteristic-changed area. It is understood that when an energy per pulse was increased, a characteristic-changed area extends towards the upstream side of the laser beam. When an energy per pulse was 1.8 $\mu$J/pulse, 2.3 $\mu$J/pulse, 2.8 $\mu$J/pulse, 3.5 $\mu$J/pulse and 4.4 $\mu$J/pulse, the length of a characteristic-changed area was 450 $\mu$m, 500 $\mu$m, 800 $\mu$m, 900 $\mu$m and 1000 $\mu$m.

When an energy per pulse was 0.9 to 1.8 $\mu$J/pulse, one thread-like characteristic-changed area was formed. However, when an energy per pulse was 2.3 to 7.0 $\mu$J/pulse, a characteristic-changed area formed at this time was like a plurality of thread-like portions bound together. Here, in order to form a characteristic-changed area consisting of one thread-like portion, it is preferable for an energy per pulse to be set at 0.9 to 1.8 $\mu$J/pulse.

On the other hand, when an energy per pulse was larger than 10 $\mu$J/pulse, a characteristic-changed area became such that granular portions were randomly arranged along an optical-axis of a laser beam. Accordingly, in order to form a thin thread-like characteristic-changed area, it is preferable for an energy per pulse to be set at 10 $\mu$J/pulse or less.

Moreover, it has been understood that in order to form a characteristic-changed area consisting of one thread-like portion, there have been respectively preferable ranges in both NA and an energy per pulse. Some preferable values for an energy per pulse when NA is 0.05, 0.1 and 0.3, are 1.1 to 2.3 $\mu$J/pulse, 0.9 to 2.0 $\mu$J/pulse, and 0.3 to 0.5 $\mu$J/pulse, respectively.

When a characteristic-changed area is formed under the above condition, an increased exposure time will produce a characteristic-changed area having an elongated length. On the other hand, it has been understood that once an exposure time reaches a certain length, the length of a characteristic-changed area will arrive at its saturated state. In detail, when NA is 0.05, a saturation time is 30 minutes and the length of a characteristic-changed area at this time is 500 $\mu$m. When NA is 0.1, a saturation time is 10 minutes and the length of a characteristic-changed area at this time is 200 $\mu$m. When NA is 0.3, a saturation time is 5 minutes and the length of a characteristic-changed area at this time is 40 μm. Therefore, it is understood that if it is desired to form a characteristic-changed area having a long length, it is necessary to reduce NA.

Next, description will be given to explain a method for forming a characteristic-changed area having a desired length. Namely, at first, various values of NA and energy per pulse are used to form a characteristic-changed area within a working object. Then, an investigation was made to inspect a relationship among NA, energy per pulse and a saturated length of a characteristic-changed area. Subsequently, in accordance with this relationship, an NA and an energy per pulse are obtained which will ensure that a saturated length of a characteristic-changed area can become substantially equal to a desired length of the characteristic-changed area. By performing the laser processing under the above obtained condition, it is possible to form a characteristic-changed area having a desired length. When a characteristic-changed area has an increased length, it is allowed to improve a visibility of a mark. On the other hand, when a working object has a small thickness, it is preferable to reduce the length of a characteristic-changed area, corresponding to its thickness.

Although the above embodiments have used a pulse laser beam whose pulse width is 130 fs, it is in fact also possible to use a pulse laser beam whose pulse width is in pico second order, thereby forming a similar characteristic-changed area.

Marks formed in the above embodiments may be used as identifying marks for identifying industrial parts. Further, since industrial parts such as glass elements containing marks therein are so formed that the diffracted lights of various colors passing therethrough can be easily visualized, it is possible for these industrial parts to obtain increased values as if they are ornamental articles.

While the present invention has been described according to the above embodiments, it is to be understood that this invention should not be limited to these specific embodiments. For example, it is obviously easy for an ordinary skill in the art to make various modifications, improvements and combinations without departing from the scope as set forth in the appending claims.

What is claimed is:

1. A marking method comprising:

a first step of irradiating a marking object by a pulse laser beam while at the same time changing NA of an objective lens and an energy per pulse, thereby forming a characteristic-changed area by virtue of move of a light converging spot;

a second step of obtaining a relationship among the length of the characteristic-changed area, an NA and an energy per pulse;

a third step of determining the length of a characteristic-changed area to be formed;

a fourth step of determining an NA and an energy per pulse, in accordance with the relationship obtained in the second step, also in accordance with the length of a characteristic-changed area to be formed; and a fifth step of converging a laser beam on the marking object to form a characteristic-changed area therein, by using the determined NA and the determined energy per pulse.

2. A marking method according to claim 1, wherein the first step uses a laser beam to conduct an exposure which is continued until the length of a characteristic-changed area becomes saturated, thereby forming a characteristic-changed area having a saturated length.

* * * * *